United States Patent
Moriya et al.

(10) Patent No.: US 8,012,303 B2
(45) Date of Patent: Sep. 6, 2011

(54) CONTAINER CLEANLINESS MEASUREMENT APPARATUS AND METHOD, AND SUBSTRATE PROCESSING SYSTEM

(75) Inventors: Tsuyoshi Moriya, Nirasaki (JP); Toshiya Matsuda, Nirasaki (JP)

(73) Assignee: Tokyo Eletctron Limited, Tokyo (JP)

( * ) Notice: Subject to any disclaimer, the term of this patent is extended or adjusted under 35 U.S.C. 154(b) by 268 days.

(21) Appl. No.: 12/199,960

(22) Filed: Aug. 28, 2008

(65) Prior Publication Data

US 2009/0064760 A1    Mar. 12, 2009

Related U.S. Application Data (60) Provisional application No. 60/991,808, filed on Dec. 3, 2007.

(30) Foreign Application Priority Data

Sep. 7, 2007   (JP) .................................. 2007-232644

(51) Int. Cl.
    *H01L 21/00* (2006.01)
(52) U.S. Cl. ................. 156/345.24; 156/345.33; 15/345
(58) Field of Classification Search .................. 15/300.1, 15/302, 303, 304, 312, 314, 322, 330, 345, 15/347, 405, 409; 134/21; 156/345.24, 345.33
    See application file for complete search history.

(56) References Cited

U.S. PATENT DOCUMENTS

| | | | | | |
|---|---|---|---|---|---|
| 2,012,640 | A | * | 8/1935 | Shipman | 15/346 |
| 4,601,082 | A | * | 7/1986 | Kurz | 15/319 |
| 4,872,920 | A | * | 10/1989 | Flynn et al. | 134/21 |
| 5,238,503 | A | * | 8/1993 | Phenix et al. | 134/37 |
| 2002/0029791 | A1 | * | 3/2002 | Matsuoka | 134/18 |

OTHER PUBLICATIONS

"FOUP Cleaning System" on the web page of Technovision Inc., searched Aug. 6, 2007, 5 pages, <URL:http://www.techvision.co.jp/products/foup.htm>.

* cited by examiner

*Primary Examiner* — Michael Barr
*Assistant Examiner* — Saeed T Chaudhry
(74) *Attorney, Agent, or Firm* — Oblon, Spivak, McClelland, Maier & Neustadt, L.L.P.

(57) ABSTRACT

A container cleanliness measurement apparatus capable of preventing particles from being adhered to substrates, while improving the operation efficiency of a container for housing substrates. An FOUP inspection apparatus includes a particle-separation promoting nozzle for promoting separation of particles adhered to an inner wall of an FOUP and to carries for holding peripheral portions of wafers inside the FOUP, a particle collecting nozzle for collecting particles separated from the inner wall of the FOUP, etc., and a particle counter for measuring an amount of collected particles. The particle-separation promoting nozzle and the particle collecting nozzle constitute a probe nozzle which is adapted to enter inside the FOUP.

17 Claims, 9 Drawing Sheets

CONTAINER CLEANLINESS MEASUREMENT APPARATUS AND METHOD, AND SUBSTRATE PROCESSING SYSTEM

BACKGROUND OF THE INVENTION

1. Field of the Invention

This invention relates to a container cleanliness measurement apparatus and method, and a substrate processing system. More particularly, this invention relates to a container cleanliness measurement apparatus for use with a container for housing substrates so as to be isolated from a surrounding environment.

2. Description of the Related Art

In a semiconductor device manufacturing factory, there are installed in a clean room a plurality of substrate processing apparatuses between which semiconductor wafers (hereinafter referred to as "wafers") are transferred. To prevent dusts floating in the clean room from adhering to wafers that are being transferred, the wafers are received in a container, for example, in an FOUP (front opening unified pod), so as to be isolated from a surrounding environment.

Figure 9A:
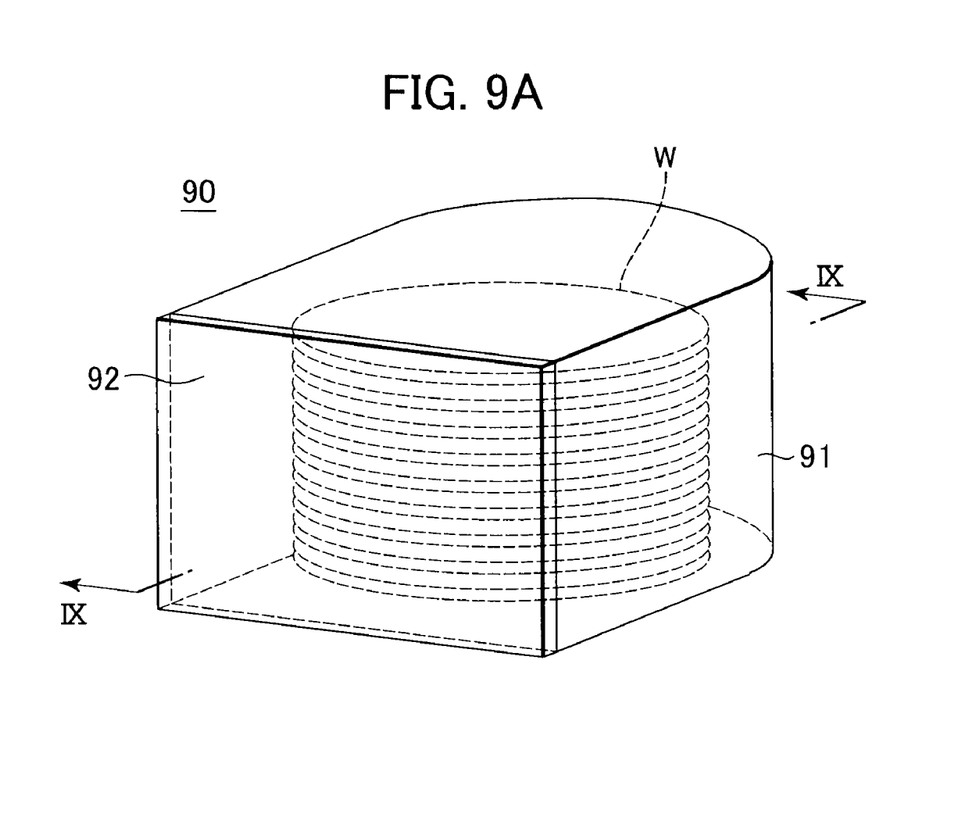
FIG. 9A is a perspective view schematically showing the construction of an FOUP shown in FIG. 8.
Figure 9B:
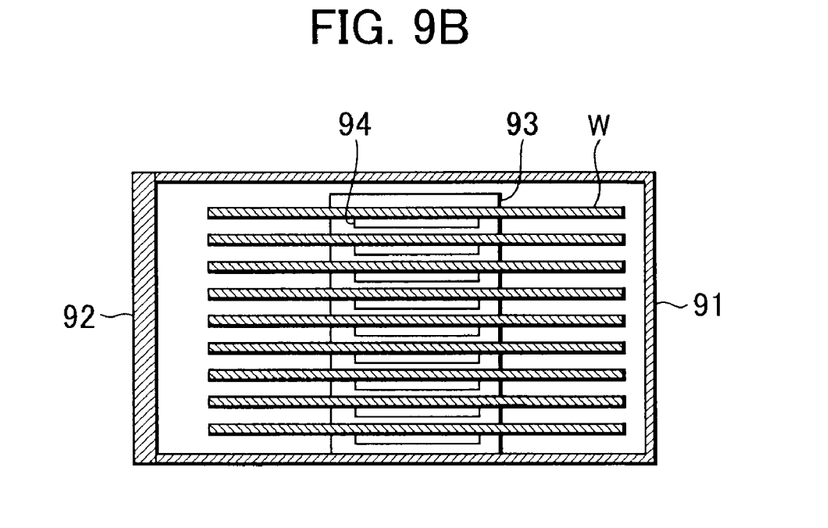
FIG. 9B is a section view of the FOUP taken along line IX-IX in FIG. 9A.

As shown in FIG. 9A, the FOUP 90 is a container which is extruded into a U-shape as seen from above. The FOUP 90 includes a body 91 having a curved side surface and an opposite open side surface, and a lid 92 disposed to face an opening in the open side surface of the body 91 and adapted to open and close the opening. The lid 92 has a seal rubber of NBR or the like and is in close contact at its periphery with the body 91 via the seal rubber. The body 91 and the lid 92 are made of ABS or other resin. The body 91 has a plurality of plate-like carriers 94 extending from an inner wall surface of the body 91 toward a center part thereof and disposed parallel to one another (FIG. 9B).

The carriers 94 hold outer peripheral portions of rear surfaces of a plurality of wafers W when the wafers are housed in the FOUP 90. Thus, the wafers W are housed in the FOUP 90 so as to extend parallel to one another.

The present inventors confirmed the following. When plasma processing such as etching is performed on a wafer W, particles are adhered to a rear surface of the wafer W and deposits are adhered to a bevel portion thereof. Particles and deposits separated from wafers of a certain lot housed in the FOUP 90 are sometimes adhered to an inner wall surface of the body 91 and to the carriers 94. In a state that wafers W of the next lot are housed in the FOUP 90, the particles, etc. adhered to the inner wall surface of the body 91 and to the carriers 94 are separated therefrom and adhered to (secondarily contaminate) the wafers W of the next lot.

The particles, etc. adhered to the wafers W function as a micromask in etching and CVD processing, which causes problems with semiconductor devices. To obviate this, there has been developed a cleaning system for cleaning an FOUP in which processing on wafers of a certain lot is completed (see, for example, the following online article).

"FOUP cleaning system" on the web page of Technovision Inc., searched Aug. 6, 2007 on the Internet <URL:http://www.techvision.co.jp/products/foup.htm>

In this cleaning system, the entire FOUP 90 is cleaned using pure water and then dried to remove particles, etc. adhered to the inner wall surface of the FOUP and to the carriers 94.

Conventionally, however, whether or not the FOUP 90 must be cleaned is determined based only on the use time of the FOUP. Therefore, the FOUP 90 is cleaned even when substantially no particles, etc. are adhered to the inner wall surface of the FOUP 90 and to the carriers 94, i.e., even when there is substantially no possibility of secondary contamination. This results in a reduction in operation efficiency of the FOUP 90, which poses a problem.

In some cases, the FOUP 90 cannot be adequately cleaned with the cleaning system. Nevertheless, there is no means for confirming whether or not adequate cleaning has been performed. When the FOUP 90 not adequately cleaned is used again, there occurs a problem of secondary contamination.

The above problems are caused by the inability of accurate measurement of the cleanliness of the FOUP 90, i.e., the inability of measurement of an amount of particles adhered to the inner wall surface of the FOUP 90 and to the carriers 94.

SUMMARY OF THE INVENTION

The present invention provides a container cleanliness measurement apparatus and method and a substrate processing system which are capable of preventing particles from being adhered to substrates, while improving the operation efficiency of a container in which the substrates are housed.

According to a first aspect of this invention, there is provided a container cleanliness measurement apparatus comprising a separation promoting unit adapted to promote separation of particles, a collection unit adapted to collect separated particles, and a measurement unit adapted to measure an amount of collected particles, wherein the separation promoting unit and the collection unit are adapted to enter inside a container which is adapted to house substrates.

With the container cleanliness measurement apparatus, separation of particles is promoted and separated particles are collected by respective ones of the separation promoting unit and the collection unit that enter inside the container in which substrates are housed. Then, an amount of the collected particles is measured by the measurement unit. It is therefore possible to accurately measure an amount of particles adhered to an inner wall of the container and to substrate carriers disposed inside the container. As a result, the container in which there are substantially no particles, etc. adhered to the container's inner wall or to the substrate carriers can be prevented from being cleaned, and whether or not the container has adequately been cleaned can be determined to prevent the container not adequately cleaned from being used again. As a consequence, particles can be prevented from being adhered to substrates, while improving the operation efficiency of the container for housing substrates.

The separation promoting unit and the collection unit can each be formed into an elongated nozzle shape having an opening formed therein.

In that case, the separation promoting unit and the collection unit each formed into an elongated nozzle shape having an opening are able to enter inside the container. It is therefore possible to measure an amount of adhered particles at a desired place in the container.

The opening of the collection unit can be formed to surround the opening of the separation promoting unit.

In that case, the opening of the collection unit surrounds the opening of the separation promoting unit, and therefore, even when particles are scattered after being separated by the separation promoting unit, a particle-scattering region is mostly within the opening of the collection unit. Thus, the scattered particles can positively be collected by the collection unit through its opening, and an amount of particles can be measured with accuracy.

The separation promoting unit can be adapted to inject at least water vapor.

In that case, since the separation promoting unit injects at least water vapor, water molecules in the water vapor enter into between particles and the container's inner wall or the substrate carriers, thereby increasing distances between the particles and the inner wall, etc. Since van del Waals forces and electrostatic forces acting as attraction forces on the particles and the inner wall, etc. are in inversely proportion to the distances therebetween, the water molecules in the water vapor are able to decrease the attraction forces acting on the particles and the inner wall, etc., thereby promoting the separation of the particles.

The collection unit can be connected to an exhaust apparatus, and a moisture collection unit can be disposed between the collection unit and the exhaust apparatus.

In that case, since the moisture collection unit is disposed between the collection unit and the exhaust apparatus, moisture can be removed from particles to which are adhered water molecules, etc. of water vapor injected from the separation promoting unit. This makes it possible to prevent the moisture from flowing into the exhaust apparatus and eroding component parts of the exhaust apparatus.

The separation promoting unit can be adapted to inject heated gas.

In that case, since the separation promoting unit injects heated gas, it is possible to generate thermal stress due to a difference between a thermal expansion coefficient of particles and that of the inner wall of the container or the substrate carriers in the container, whereby the particle separation can be promoted.

The separation promoting unit can be adapted to inject a substance with two possible phase states of gas and liquid phases or of gas and solid phases.

In that case, the separation promoting unit injects a substance with two possible phase states of gas and liquid phases or of gas and solid phases. The injected substance in a gas phase state produces, on surfaces of the container's inner wall and the substrate carriers, a boundary layer in which the substance in the gas phase state does not flow. On the other hand, the substance in a liquid or solid phase state is able to enter the boundary layer and collide with particles to provide a physical shock thereto. This impactive force can promote the particle separation.

The separation promoting unit can be adapted to inject gas while varying a flow speed of the gas like a pulsed wave.

In that case, since the separation promoting unit injects gas while varying the flow speed thereof like a pulsed wave, a variation in gas pressure can be generated, thereby increasing a physical shock which the gas applies to particles adhered to the container's inner wall and to the substrate carriers. This makes it possible to promote the particle separation.

The separation promoting unit and the collection unit can be adapted to scan a region of a predetermined area.

In that case, since a region of a predetermined area is scanned by the separation promoting unit and the collection unit, an amount of particles adhered to the container's inner wall and the substrate carriers can be measured at a plurality of places in the container, whereby the reliability of particle amount measurement can be improved.

The measurement unit can be adapted to observe scattered light generated by laser light irradiation onto the collected particles.

In that case, the measurement unit for observing scattered light generated by laser light irradiation onto the collected particles can be constituted only by a laser light irradiation unit and a scattered light observation unit, thus making it possible to simplify the construction of the measurement unit. As a result, the cost of the container cleanliness measurement apparatus can be reduced.

The measurement unit can include a flow path adapted to permit the collected particles to flow therethrough and having a bent portion, and a pressure-sensitive device disposed in the bent portion of the flow path.

In that case, the measurement unit includes a flow path permitting transported particles to flow therethrough and having a bent portion, and a pressure-sensitive device disposed in the bent portion of the flow path. The gas flow for particle transportation flows along the bent portion, whereas particles applied with an inertia force do not flow along the bent portion and collide with pressure-sensitive device disposed in the bent portion. At that time, an impactive force only due to the collision of particles is measured by the pressure-sensitive device. It is therefore possible to selectively carry out the measurement only on the particles.

According to a second aspect of this invention, there is provided a substrate processing system including a substrate receiving apparatus adapted to receive substrates by being connected with a container which is adapted to house the substrates, and a substrate processing apparatus adapted to perform processing on the received substrates, wherein the substrate receiving apparatus includes a separation promoting unit adapted to promote separation of particles, and a collection unit adapted to collect separated particles, the separation promoting unit and the collection unit are adapted to enter inside the container connected to the substrate receiving apparatus, and the substrate processing system further includes a measurement unit adapted to measure an amount of collected particles.

With the substrate processing system of this invention, the separation of particles is promoted and separated particles are collected by respective ones of the separation promoting unit and the collection unit that enter inside the container in which substrates are housed, and an amount of collected particles is measured by the measurement unit, whereby an amount of particles adhered to the container's inner wall and to substrate carriers disposed in the container can be measured with accuracy. It is therefore possible to prevent particles from being adhered to substrates while improving the operation efficiency of the container for housing substrates. Since the substrate receiving apparatus connected to the container includes the separation promoting unit and the collection unit, an amount of particles adhered to the container's inner wall and to the substrate carriers can be measured, with the container kept connected to the substrate receiving apparatus. As a result, the amount of particles adhered to the container's inner wall, etc. can be measured while processing is being performed by the substrate processing apparatus on a substrate, which is transferred out from the container by the substrate receiving apparatus. Therefore, the measurement can efficiently be carried out.

The substrate processing apparatus can perform any one of etching, CVD, heat treatment, diffusion processing, and substrate cleaning.

According to a third aspect of this invention, there is provided a container cleanliness measurement method for measuring cleanliness inside a container which is adapted to house substrates, comprising a separation promoting step of promoting separation of particles, a collection step of collecting separated particles, and a measurement step of measuring collected particles.

With the container cleanliness measurement method, particle separation is promoted, separated particles are collected, and an amount of collected particles is measured, and therefore, an amount of particles can accurately be measured. This makes it possible to prevent the container from being cleaned, in which substantially no particles, etc. are adhered to the container's inner wall and to the substrate carriers disposed inside the container, and confirm whether or not the container has adequately been cleaned to thereby make it possible to prevent the container not adequately cleaned from being used again. As a result, it is possible to prevent particles from being adhered to substrates, while improving the operation efficiency of the container for housing the substrates.

The separation promoting step and the collection step can be repeated.

In that case, since the separation promoting step and the collection step are repeated, it is ensured that particles are separated and the separated particles are collected, whereby the reliability of particle amount measurement can be improved.

The separation promoting step and the collection step can each be carried out at least once when the measured amount of particles is equal to larger than a predetermined reference value.

In that case, when the measured amount of particles is not less than the predetermined reference value, the separation promoting step and the collection step are each performed at least once. It is therefore possible to clean the container by removing particles adhered to the container's inner wall and to the substrate carriers in succession to the particle amount measurement.

The container cleanliness measurement method can include a receiving confirmation step of confirming, prior to the separation promoting step, whether nor not the substrates are housed in the container, and the separation promoting step can be carried out when the substrates are not housed in the container.

In that case, since the separation promoting step is carried out when substrates are not housed in the container, particles separated in the separation promoting step but not collected in the collection step can be prevented from being adhered to the substrates.

Further features of the present invention will become apparent from the following description of exemplary embodiments with reference to the attached drawings.

DETAILED DESCRIPTION OF THE PREFERRED EMBODIMENTS

The present invention will now be described in detail below with reference to the drawings showing preferred embodiments thereof.

First, a container cleanliness measurement apparatus according to a first embodiment of this invention will be described.

Figure 1:
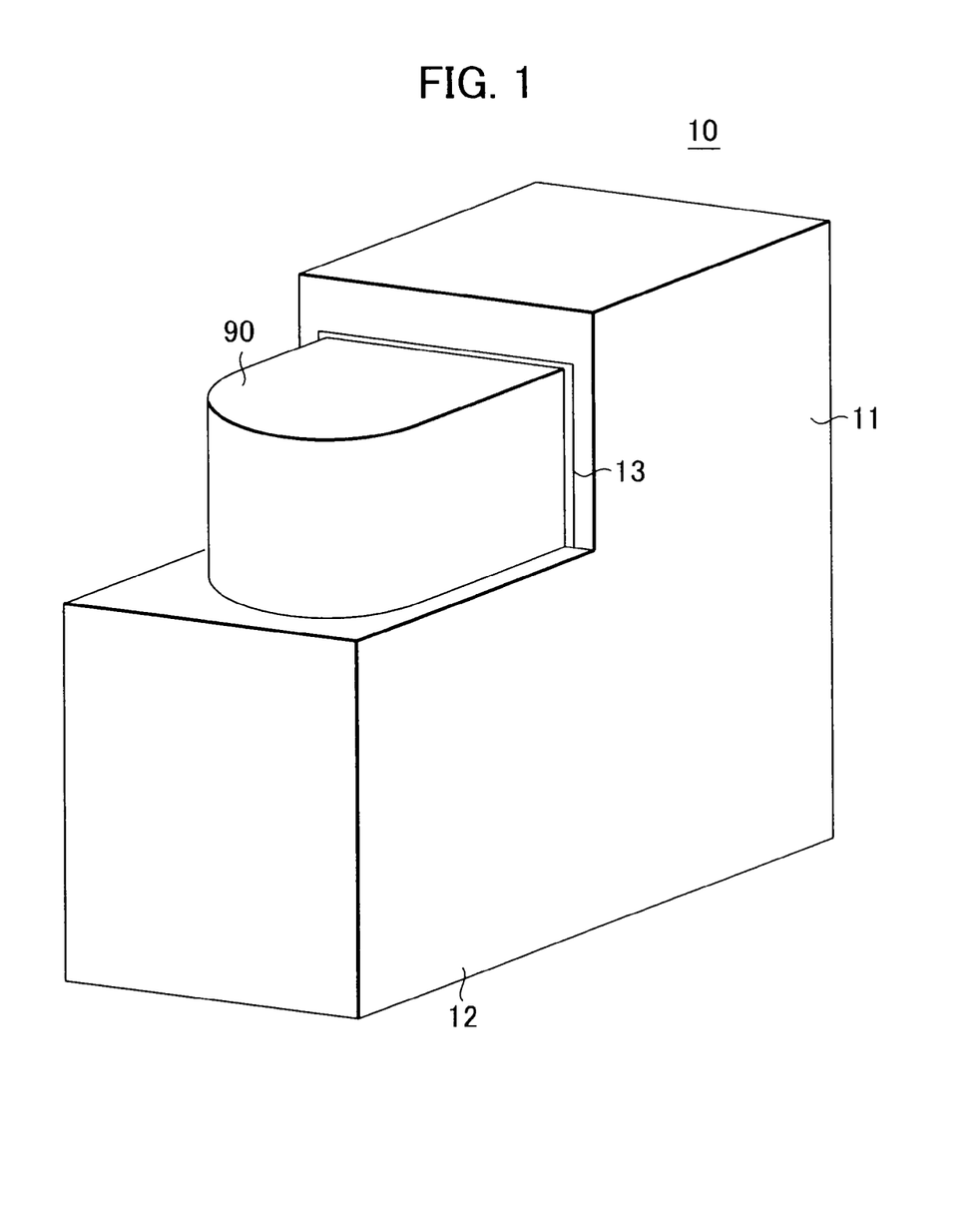
FIG. 1 is a perspective view schematically showing the external construction of an FOUP inspection apparatus as a container cleanliness measurement apparatus according to a first embodiment of this invention.
Figure 2:
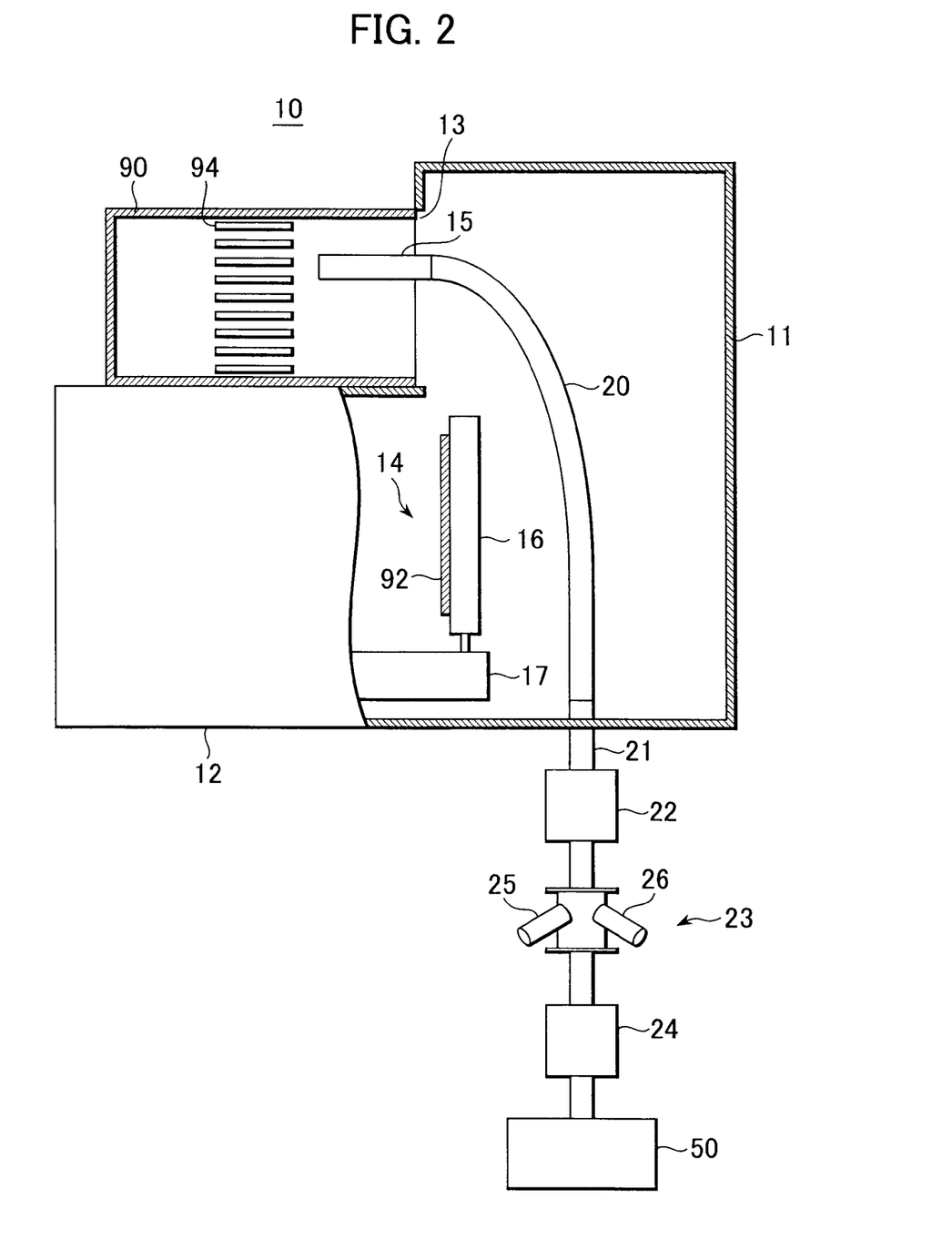
FIG. 2 is a fragmentary section view schematically showing the internal construction of the FOUP inspection apparatus shown in FIG. 1.

FIG. 1 schematically shows in perspective view the external construction of an FOUP inspection apparatus 10 as the container cleanliness measurement apparatus of this embodiment, and FIG. 2 schematically shows in fragmentary section view the internal construction of the FOUP inspection apparatus 10.

As shown in FIG. 1, the FOUP inspection apparatus 10 includes a box-like apparatus body 11 and a box-like FOUP mounting part 12 which is lower in height than the body 11. The FOUP mounting part 12 has an upper surface on which an FOUP 90 is placed, and functions as a mounting table. The inspection apparatus body 11 is formed at its side surface with a rectangular opening 13 facing the FOUP 90 placed on the FOUP mounting part 12. The opening 13 is larger in size than a lid 92 of the FOUP 90. Thus, the lid 92 is able to enter inside the body 11 to which is connected the FOUP 90 placed on the FOUP mounting part 12.

As shown in FIG. 2, the FOUP inspection apparatus 10 includes an FOUP opener 14 and a probe nozzle 15, which are both disposed within the inspection apparatus 10. The FOUP opener 14 includes a lid holder 16 adapted to hold the lid 92 entering inside the body 11, and a base 17 which is movable up and down and on which the lid holder 16 is mounted vertically. When the base 17 is moved downward, with the lid 92 held by the lid holder 16, the lid 92 is taken off from the FOUP 90, whereby the inside of the FOUP 90 is communicated with the inside of the inspection apparatus body 11.

Figure 3A:
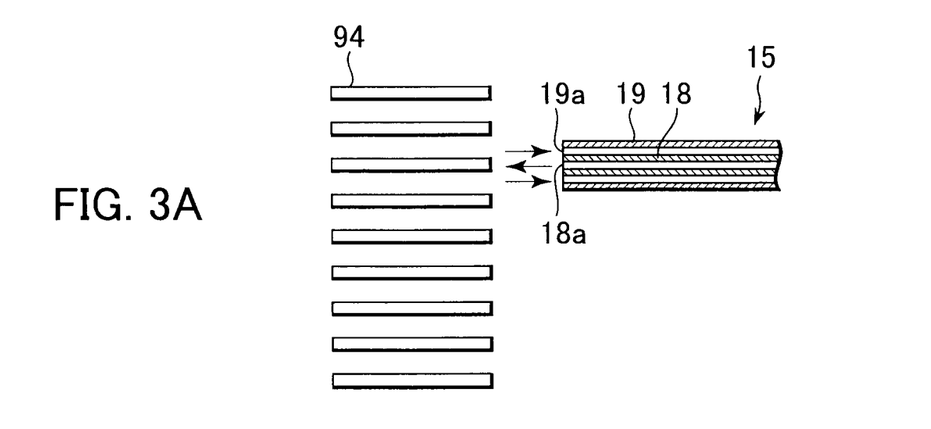
FIG. 3A is an enlarged view showing the construction of a probe nozzle in FIG. 2.

In a state where the inside of the FOUP 90 is communicated with the inside of the body 11, the probe nozzle 15 enters inside the FOUP 90 to face a measurement object part inside the FOUP 90 such as, for example, a part of an inner wall of the FOUP 90 or carriers 94. As shown in FIG. 3A, the probe nozzle 15 includes a particle-separation promoting nozzle 18 (separation promoting unit) and a particle collecting nozzle 19 (collection unit), which are elongated nozzles each having an opening 18a or 19a formed therein. The particle collecting nozzle 19 is larger in diameter than the particle-separation promoting nozzle 18. These nozzles 18, 19 are disposed parallel to each other and the particle collecting nozzle 19 is disposed to surround the particle-separation promoting nozzle 18, and therefore, the nozzles 18, 19 form a double tube structure. The opening 19a of the particle collecting nozzle 19 surrounds the opening 18a formed in the particle-separation promoting nozzle 18. The particle collecting nozzle 19 has an outer diameter of about 1 cm to 2 cm.

Figure 3B:
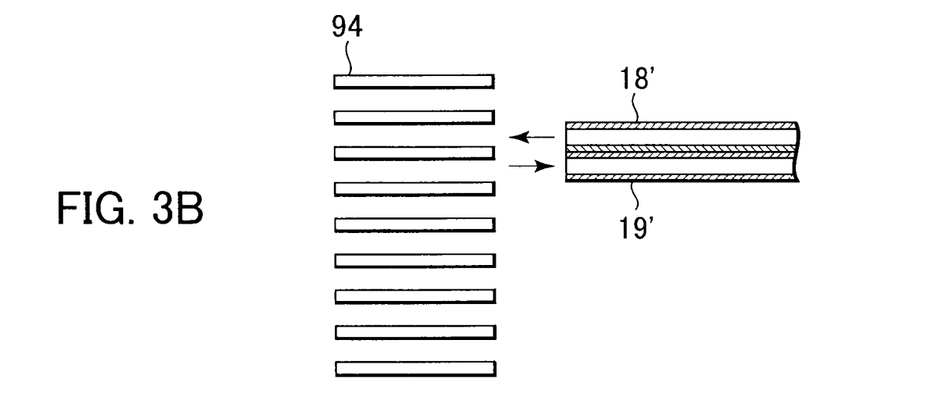
FIG. 3B is an enlarged view of a probe nozzle according to a first modification.

It should be noted that the relation in the probe nozzle 15 between the particle-separation promoting nozzle and the particle collecting nozzle is not limited to the above described one. For example, a particle-separation promoting nozzle 18' and a particle collecting nozzle 19', which are nearly the same in diameter, may be disposed side-by-side (FIG. 3B).

The particle collecting nozzle 19 is connected via a flexible tube 20 and a pipe 21 to an exhaust apparatus 50 disposed outside the FOUP inspection apparatus 10. When the exhaust apparatus operates to evacuate gas and the like in the FOUP 90 via the pipe 21, the flexible tube 20, and the probe nozzle 15, particles floating inside the FOUP 90 are sucked together with the gas in the FOUP 90 and collected by the particle collecting nozzle 19.

In a state where the probe nozzle 15 faces the measurement object part, the particle-separation promoting nozzle 18 injects a substance for promoting the particle separation toward the measurement object part, thereby promoting the particle separation from the measurement object part. The particle collecting nozzle 19 collects particles that are separated from the measurement object part and scattered around.

To separate particles adhered to the inner wall of the FOUP 90, etc., gas is ordinarily blown to the inner wall, etc. at a high speed. At that time, a boundary layer is produced on a surface of the inner wall, etc. It was known that gas hardly flows inside the boundary layer. Since a large particle partly projects from the boundary layer, the large particle is made in contact with the high speed gas flow, and is separated from the inner wall, etc. by being applied with a viscous force from the gas. On the other hand, a small particle which does not project from the boundary layer is not applied with a viscous force from the gas, and is not separated from the inner wall, etc. As a result, small particles adhered to the inner wall, etc. cannot be collected. Even if particles separated by the action of the high speed gas flow are collected for the measurement of an amount of separated particles, the measured amount does not accurately represent an amount of particles adhered to the inner wall, etc.

In this embodiment, to separate all the particles from the inner wall, etc. irrespective of particle sizes, particle separation is carried out without forming the boundary layer on the surface of the inner wall, etc.

FIG. 4A to FIG. 4D show in process diagrams how particles are separated in this embodiment.

Figure 4A:
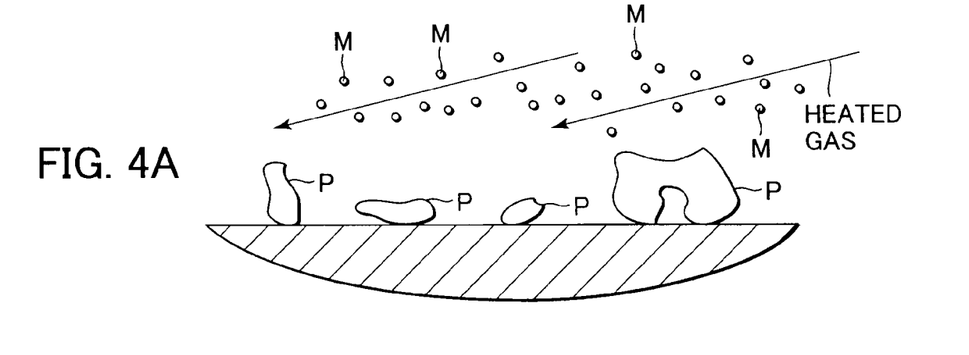
FIG. 4A to FIG. 4D are process diagrams showing how particles are separated in the first embodiment.
Figure 4B:
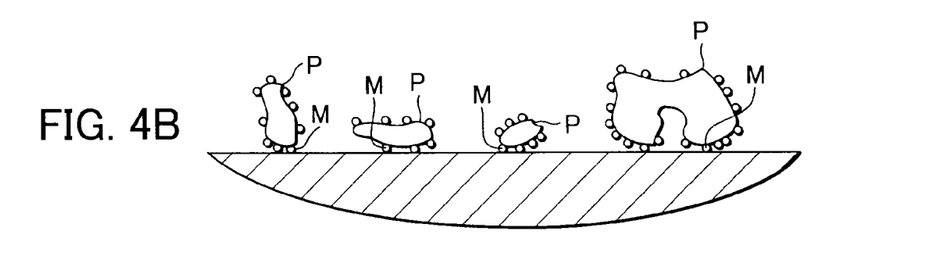
Figure 4C:
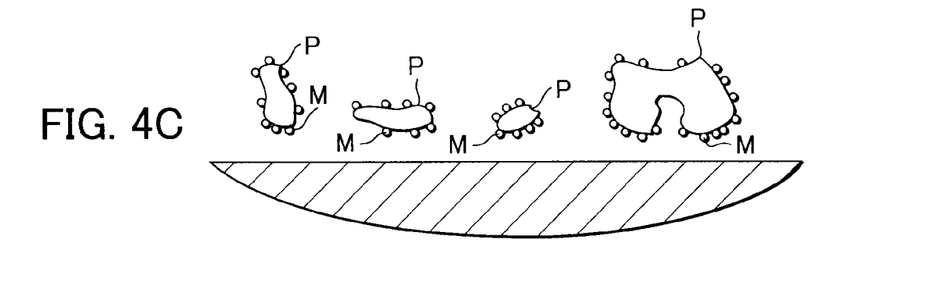

As shown in FIG. 4A, the particle-separation promoting nozzle 18 injects water vapor, which is mixed as particle separation promoting substance in heated gas, toward the measurement object part at a low speed. Water molecules M and clusters (not shown) thereof in the injected water vapor enter into between particles P and the measurement object part (the inner wall of the FOUP 90 and/or the carriers 94), to thereby increase distances between the particles P and the measurement object part (FIG. 4B). Usually, an attraction force acting on a particle and the measurement object part corresponds to van der Waals force or electrostatic force. The van der Waals force and the electrostatic force are each inversely proportional to a distance between the particle and the measurement object part (For example, the electrostatic force is inversely proportional to the square of the distance, and the van der Waals force is inversely proportional to the distance to the sixth power). Water molecules M and clusters contained in water vapor increase the distances between particles P and the measurement object part, and therefore act to decrease attraction forces acting on the particles P and the measurement object part, thereby promoting separation of the particles P from the measurement object part (FIG. 4C).

Figure 4D:
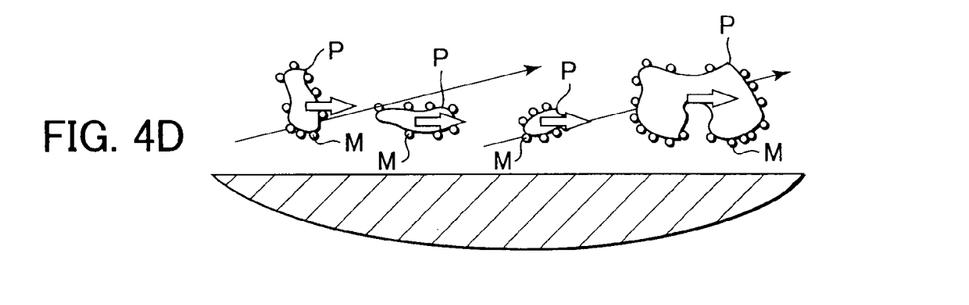

Subsequently, the particles P separated from the measurement object part are sucked and collected by the particle collecting nozzle 19 (FIG. 4D).

Since the heated gas including the water vapor is injected at a low speed from the particle-separation promoting nozzle 18, a boundary layer is not formed on a surface of the measurement object part. As a result, the water molecules M and the clusters contained in the water vapor enter into between the measurement object part and all the particles P adhered to the measurement object part, thereby promoting the separation of all the particles P.

Since the separation of all the particles P adhered to the measurement object part is promoted as described above, the particle collecting nozzle 19 is able to collect all the particles P adhered to the measurement object part. Thus, an amount of the particles P adhered to the measurement object part can accurately be measured by simply measuring an amount of the particles P collected by the particle collecting nozzle 19.

The smaller the sizes of clusters contained in the injected water vapor, the more easily the clusters will be able to enter into between the particles P and the measurement object part. It is therefore preferable that the clusters contained in the injected water vapor be small in size. Instead of injecting heated gas mixed with water vapor, a simple water vapor may be injected by the particle-separation promoting nozzle 18. Nevertheless, by mixing water vapor into the heated gas, it is possible to reduce a possibility of the water vapor being condensed due to a reduction in temperature. Accordingly, the water vapor mixed in the heated gas is suitable for use as the separation promoting substance injected by the particle-separation promoting nozzle 18.

The particle separation promoting substance injected by the nozzle 18 toward the measurement object part is not limited to the water vapor mixed in the heated gas. As the separation promoting substance, there may be mentioned a simple substance of low-speed heated gas, a substance having two possible phase states of gas and liquid phases or of gas and solid phases (for example, aerosol of carbon dioxide or of water), a gas having a flow speed varying like a pulsed wave, and so on.

By injecting a simple substance of low-speed heated gas by the particle-separation promoting nozzle 18 toward the measurement object part, it is possible to produce thermal stress resulting from a difference in thermal expansion coefficient between particles and the measurement object part, whereby the separation of particles P can be promoted. Even if a boundary layer is formed on a surface of the measurement object part, heat is conveyed to the particles P without relation to the presence of the boundary layer, and therefore the separation of all the particles P can be promoted.

For a case where thermal stress is utilized for the separation of particles P from the measurement object part, the measurement object part may be heated, for example, by heat irradiation from a lamp heater, instead of injecting the heated gas. Also in that case, there can be produced thermal stress due to a difference in thermal expansion coefficient between the particles and the measurement object part.

In the case that a substance having two possible phase states of gas and liquid phases or of gas and solid phases is injected by the particle-separation promoting nozzle 18 toward the measurement object part, the injected substance in gas phase state produces a boundary layer on a surface of the measurement object part. On the other hand, since being heavy in mass, the substance in a liquid or solid phase state is able to enter the boundary layer and collide with particles P to give a physical shock. The resultant impactive force can promote the separation of all the particles P.

When a gas having a flow speed varying like a pulsed wave is injected by the particle-separation promoting nozzle 18 toward the measurement object part, a pressure variation is produced by the injected gas, and a large physical shock is given to the particles P adhered to the measurement object part. As a result, the separation of the particles P can be promoted.

For a case where a gas with pressure variation is utilized, a gas to be utilized is not limited to the gas having a flow speed varying like a pulsed wave, but may be a gas with ultrasonic vibration or high-frequency vibration.

Some of the above described plural types of separation promoting substances may be combined for being injected from the particle-separation promoting nozzle 18 toward the measurement object part.

Referring to FIG. 2 again, in the pipe 21 extending between the probe nozzle 15 and the exhaust apparatus, there are disposed a moisture trap 22 (moisture collection unit), a particle counter 23 (measurement unit), and a particle trap 24 in this order as viewed from the side of the probe nozzle 15.

The moisture trap 22 includes a low-temperature part (not shown) that absorbs moisture, such as for example, water molecules M and clusters thereof adhered to surfaces of the particles P flowing through the pipe 21 together with gas, whereby the moisture is removed from the particles P. It is therefore possible to prevent the moisture from flowing into the below-described particle counter 23 and the exhaust apparatus, thereby preventing corrosion of component parts of the particle counter 23 and the exhaust apparatus. If the particle counter 23 is one that utilizes laser light as described below, it is also possible to prevent a scattered light observation window from being clouded, whereby the reliability of measurement of particles P can be improved.

The particle counter 23 includes a laser light irradiation unit 25 for irradiating laser light toward the inside of the pipe 21, and a scattered light observation unit 26 for use for observation of scattered light that is produced when a particle P flowing through the pipe 21 is irradiated with the laser light. The particle counter 23 measures an amount of particles P based on the number of times the scattered light is observed and/or based on the strength of scattered light. The particles P flowing through the pipe 21 are particles P which are collected by the particle collecting nozzle 19 and which correspond to all the particles P adhered to the measurement object part. Thus, the particle counter 23 is able to measure all the particles P adhered to the measurement object part. In addition, the particle counter 23 can be constituted by the laser light irradiation unit 25 and the scattered light observation unit 26 and is therefore simple in construction. As a result, the fabrication cost of the FOUP inspection apparatus 10 can be reduced.

The particle counter 23 is not limited to the above described type in which laser light and scattered light are utilized, but may be, for example, of a type based on a DMA (differential mobility analyzer) method in which particles are charged and an electric field is generated for collection of the particles, or based on a CNC (condensation new creation counting) method in which particles are grown in growing gas for subsequent particle measurement, or based on a method in which impactive forces of particles are utilized.

Figure 5:
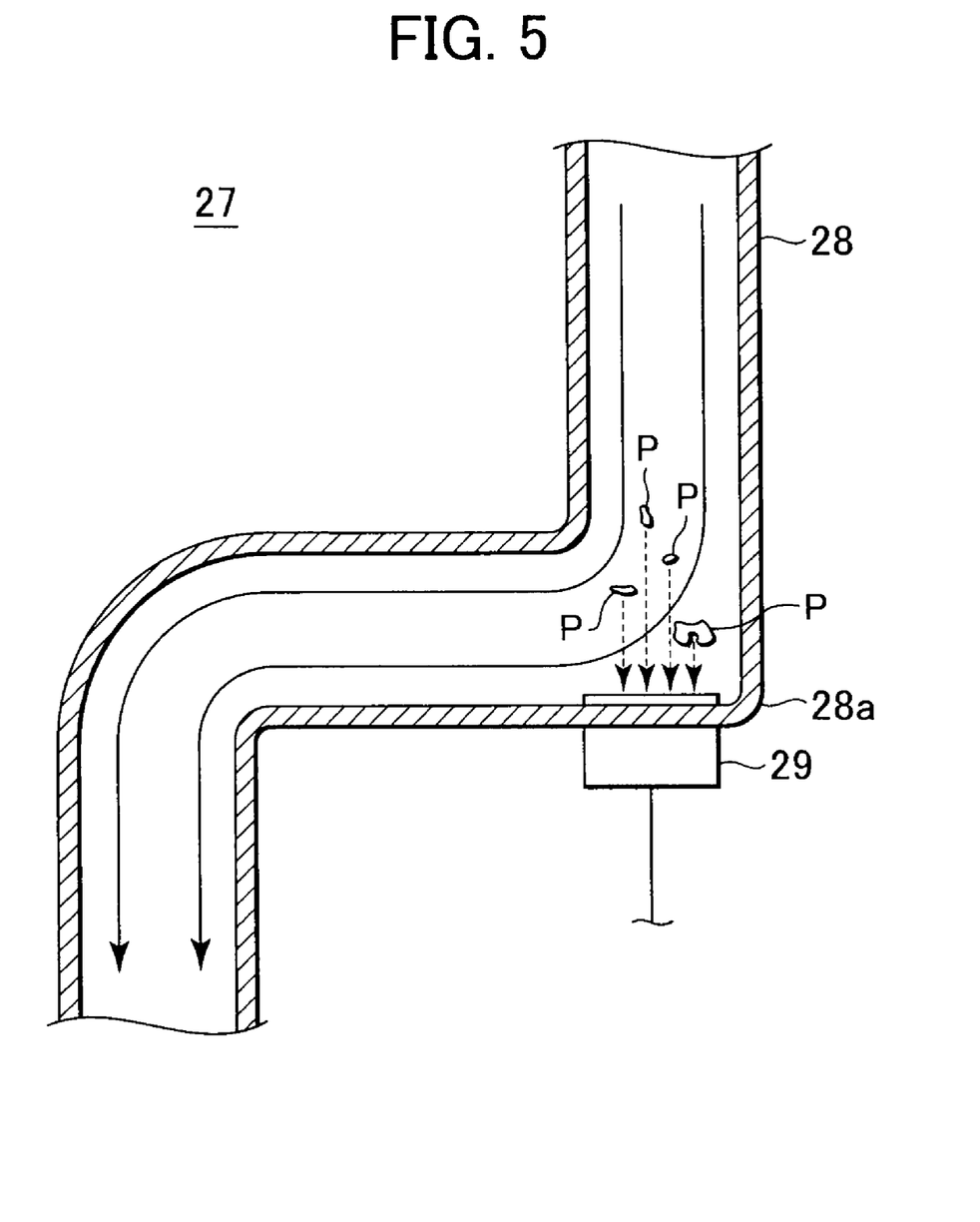
FIG. 5 is a section view schematically showing the construction of a modification of the particle counter in FIG. 2.

As shown in FIG. 5, the particle counter 27, which is of a type utilizing impactive forces of particles, includes a pipe 28 (flow path) having a bent portion 28 and permitting a gas flow for transporting particles P to pass therethrough, and a pressure-sensitive sensor 29 (pressure-sensitive device) exposed to the inside the pipe 28 at the bent portion 28a and directed toward upstream of the gas flow (shown by arrows in FIG. 5) flowing through the pipe 28.

In the particle counter 27, the gas flow flows along the bent portion 28a. On the other hand, the particles P do not flow along the bent portion 28a due to inertial forces acting thereon, but rather move rectilinearly from the upstream side of the gas flow and collide with the pressure-sensitive sensor 29. At that time, an impactive force produced upon collision is detected by the pressure-sensitive sensor 29. Since only the particles P collide with the pressure-sensitive sensor 29, the impactive force measured by the pressure-sensitive sensor 29 is caused only by the collision of particles. Therefore, the particle counter 27 is able to selectively measure the particles.

The particle trap 24 includes a filter (not shown) of mesh structure, and collects most of the particles P flowing through the pipe 21, whereby the particles P are prevented from flowing into the exhaust apparatus.

Though the measurement object part can be any part inside the FOUP 90, it is preferable that the measurement object part be set at the carriers 94 since particles P are easily transferred onto the carriers 94 with which bevel portions of wafers W are brought in contact.

The measurement object part is not limited to being set to one place, but may preferably be set at plural places from the viewpoint of improving the reliability of measurement of an amount of particles. In that case, it is preferable that the probe nozzle 15 be adapted to scan a region of a predetermined area inside the FOUP 90, whereby an amount of particles P adhered to the inner wall of the FOUP 90, etc. can easily be measured at the plural places.

Figure 3C:
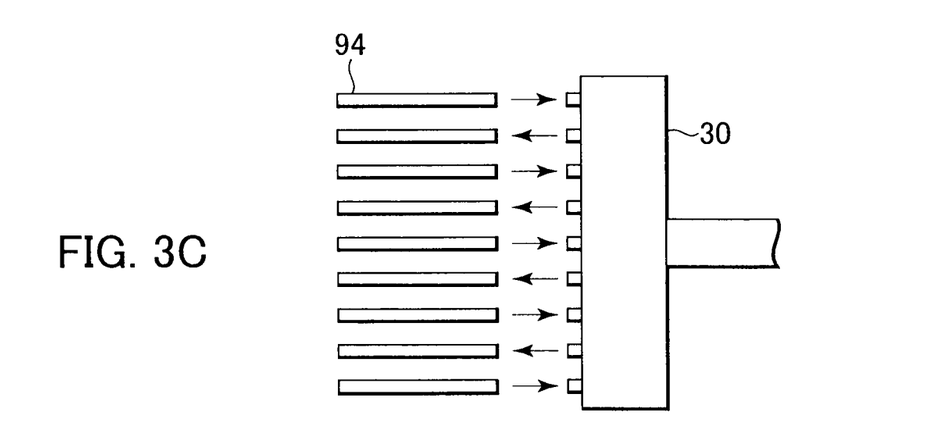
FIG. 3C is an enlarged view of a probe nozzle according to a second modification.

The particles P adhered to the inner wall, etc. may not be measured in part, but may be measured in its entirety inside the FOUP 90. In that case, the probe nozzle is preferably constituted as a shower head 30 shown in FIG. 3C.

With the FOUP inspection apparatus 10 that functions as the container cleanliness measurement apparatus according to the embodiment, the particle-separation promoting nozzle 18 and the particle collecting nozzle 19 enter inside the FOUP 90, the nozzle 18 promotes the separation of particles P from the measurement object part, and the nozzle 19 collects the separated particles P. Then, an amount of the collected particles P is measured by the particle counter 23, whereby an amount of particles P adhered to the inner wall of the FOUP 90, etc. can be measured with accuracy. This makes it possible to prevent the FOUP 90 in which substantially no particles P, etc. are adhered to the inner wall, etc. from being cleaned, and to confirm whether or not the FOUP 90 has adequately been cleaned to thereby prevent the FOUP 90 not adequately cleaned from being reused. As a result, particles P can be prevented from being adhered to wafers W, while improving the operation efficiency of the FOUP 90.

The particle-separation promoting nozzle 18 and the particle collecting nozzle 19 of the FOUP inspection apparatus 10 are each formed into an elongated nozzle shape having an opening formed therein, and are therefore able to easily enter inside the FOUP 90. As a result, an amount of particles P adhered to a prescribed part inside the FOUP 90 can be measured.

In the FOUP inspection apparatus 10, the particle collecting nozzle 19 has an opening 19a thereof formed to surround an opening 18a of the particle-separation promoting nozzle 18. Thus, even when particles P are separated and scattered by the particle-separation promoting nozzle 18, a particle-scattering region is mostly within the opening 19a of the particle collecting nozzle 19, and therefore, scattered particles can positively be collected by the particle collecting nozzle 19 through the opening 19a, whereby an amount of particles P can be measured more accurately.

Next, a container cleanliness measurement method of this embodiment will be described.

Figure 6:
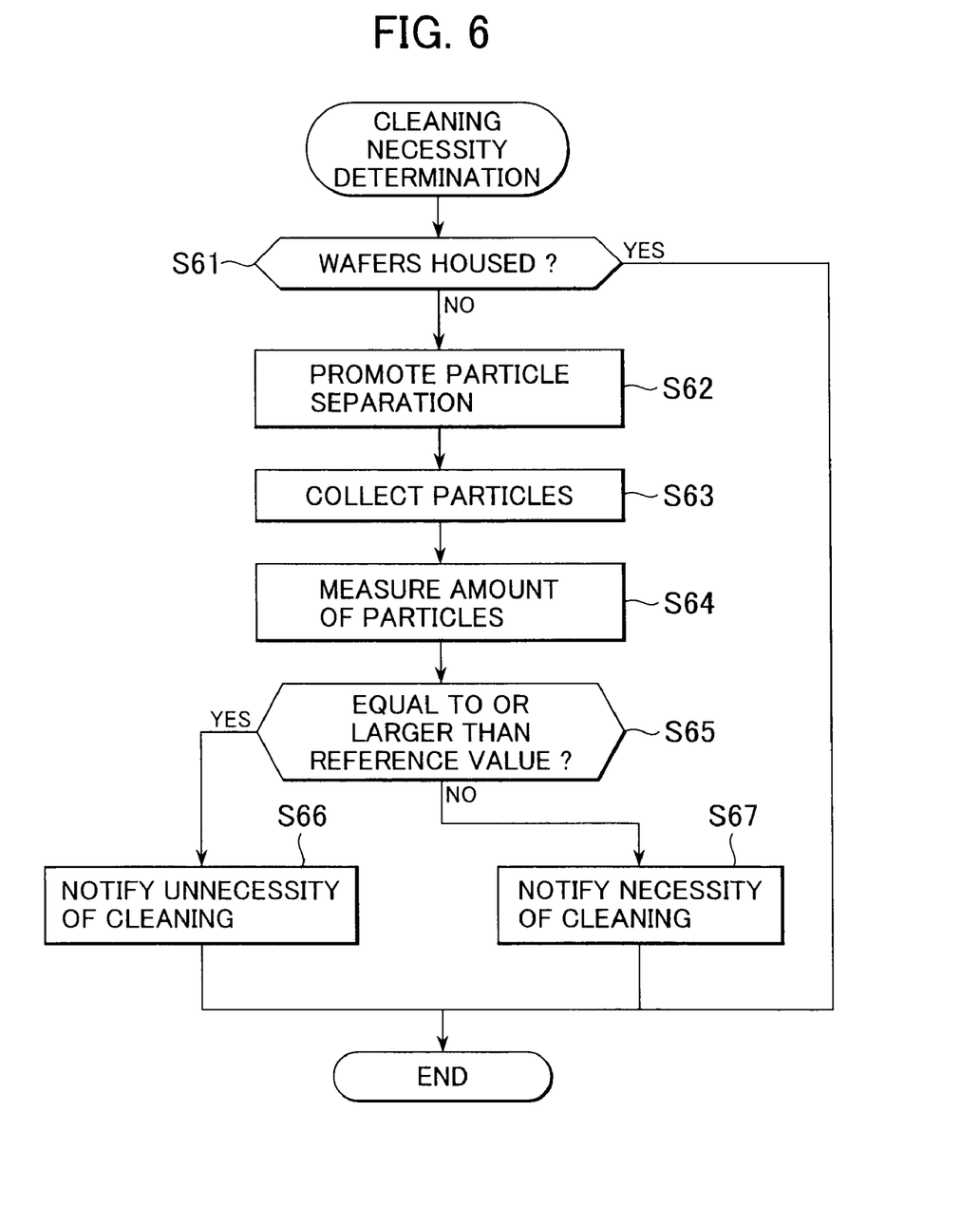
FIG. 6 is a flowchart of a process for determining the necessity of cleaning an FOUP to which a container cleanliness measurement method according to the first embodiment is applied.

FIG. 6 shows in flowchart a process for determination of the necessity for cleaning an FOUP to which is applied a container cleanliness measurement method of this embodiment. The process of FIG. 6 is carried out at regular intervals. For example, the process is carried out in the FOUP inspection apparatus 10 each time the FOUP 90, which is a measurement object, has been used to execute lot processing a predetermined number of times.

First, in connection with the process of FIG. 6, the FOUP 90 is mounted on the FOUP mounting part 12 of the FOUP inspection apparatus 10, and the inside of the FOUP 90 is communicated with the inside of the inspection apparatus body 11. Then, a wafer probe (not shown) of the inspection apparatus 10 is caused to enter inside the FOUP 90. As shown in FIG. 6, whether or not wafers W are housed in the FOUP 90 is determined by using the wafer probe (step S61) (receiving confirmation step). If it is determined that wafers W are housed in the FOUP 90 (YES to step S61), the process is completed. On the other hand, if it is determined that wafers W are not housed, the probe nozzle 15 is caused to enter inside the FOUP 90 and positioned to face the measurement object part.

Next, the particle-separation promoting nozzle 18 injects heated gas mixed with water vapor toward the measurement object part at a low speed to promote separation of particles P from the measurement object part (step S62) (separation promoting step), and the particle collecting nozzle 19 sucks and collects particles P separated from the measurement object part (step S63) (collection step).

Then, the particle counter 23 measures (counts) an amount of particles P flowing through the pipe 21 together with the gas (step S64) (measurement step). A controller (not shown) of the FOUP inspection apparatus 10 determines whether or not the measured amount of particles P is equal to or greater than a predetermined reference value, which is set in advance (step S65).

As a result of the determination in step S65, if it is determined that the measured amount of particles P is equal to or larger than the predetermined reference value (YES to step S65), it is notified via a monitor (not shown) or the like of the FOUP inspection apparatus 10 to an operator that the FOUP 90 is required to be cleaned (step S66), and the present process is completed. If, on the other hand, it is determined that the measured amount of particles P is less than the predetermined reference value, it is notified via the monitor or the like that the FOUP 90 is not required to be cleaned (step S67), and the present process is completed.

With the process of FIG. 6, the separation of particles P is promoted, separated particles P are collected, and an amount of the collected particles P is measured, whereby an amount of particles P can be measured with accuracy.

In the process of FIG. 6, since the separation of particles P from the measurement object part is promoted in a state where no wafers W are housed in the FOUP 90, it is possible to prevent particles P, which are separated but not collected by the particle collecting nozzle 19, from being adhered to wafers W.

In the process of FIG. 6, steps S62 to S64 are each executed only once. Alternatively, the steps S62 to S64 may each be repeated a predetermined number of times, whereby the separation of particles P from the measurement object part and the collection of separated particles P can be positively carried out to improve the reliability of measurement of the amount of particles P.

In the process of FIG. 6, an amount of particles P is not measured when wafers W are housed in the FOUP 90. However, by using the probe nozzle 15 for the measurement, scattered particles P can positively be collected by the particle collecting nozzle 19 as described above. In other words, there is no fear that the scattered particles P are adhered to the wafers W, even when wafers W are housed in the FOUP 90. By using the probe nozzle 15 for measurement, it is therefore possible to carry out the processing in step S62 and subsequent steps even when wafers W are housed in the FOUP 90.

In addition, the FOUP inspection apparatus 10 is able to perform simple cleaning of the FOUP 90.

Figure 7:
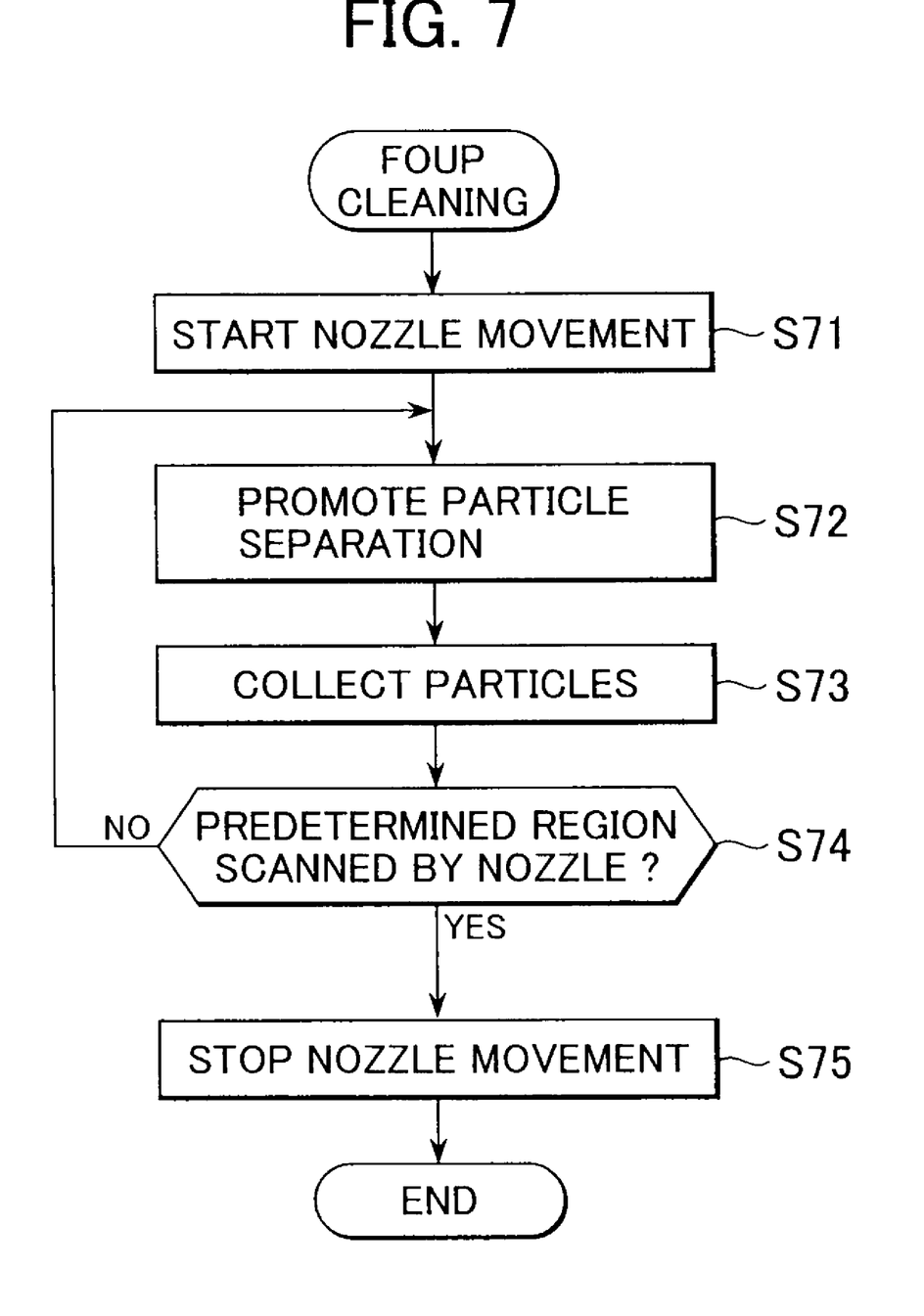
FIG. 7 is a flowchart showing an FOUP cleaning process performed by the FOUP inspection apparatus in FIG. 1.

FIG. 7 shows in flowchart an FOUP cleaning process performed by the FOUP inspection apparatus in FIG. 1. This process is carried out in succession to the process of FIG. 6, when it is determined that the amount of particles measured in step S65 in FIG. 6 is equal to or larger than the predetermined reference value.

As shown in FIG. 7, the probe nozzle 15 enters inside the FOUP 90 and starts moving within a predetermined cleaning region (step S71).

Next, the particle-separation promoting nozzle 18 injects at a low speed the water vapor mixed in the heated gas toward the inner wall of the FOUP 90, etc., to promote the separation of particles P from the inner wall, etc. (step S72). The particle collecting nozzle 19 sucks and collects particles P separated from the inner wall, etc. (step S73). As a result, particles P adhered to the inner wall, etc. are removed.

Next, the controller of the FOUP inspection apparatus 10 determines whether or not the probe nozzle 15 has scanned all the predetermined cleaning region (step S74). If it is determined that the probe nozzle 15 has not scanned all the predetermined cleaning region (No to step S74), the process returns to step S72. If, on the other hand, the all the predetermined cleaning region has been scanned, the probe nozzle 15 is stopped to move (step S75), and the present process is completed.

According to the process shown in FIG. 7, if the measured amount of particles P is equal to or larger than the predetermined reference value, the separation of particles from the inner wall, etc. is promoted, and the separated particles P are sucked and collected to thereby remove particles P adhered to the inner wall, etc. That is, particles P adhered to the inner wall, etc. are removed in succession to the measurement of amount of particles P, whereby the FOUP 90 can be cleaned. It is therefore possible to efficiently carry out the measurement of amount of particles adhered to the inner wall of the FOUP 90, etc. and the cleaning of the FOUP 90.

In the process of FIG. 7, the FOUP 90 is cleaned by the probe nozzle 15, if the measured amount of particles P is equal to or greater than the predetermined reference value. However, if the measured amount of particles P is very large, it is preferable that the FOUP 90 be cleaned by means of a cleaning system adapted to clean the entirety of the FOUP 90 as disclosed in the above described online document.

Next, a substrate processing system according to a second embodiment of this invention will be described.

Figure 8:
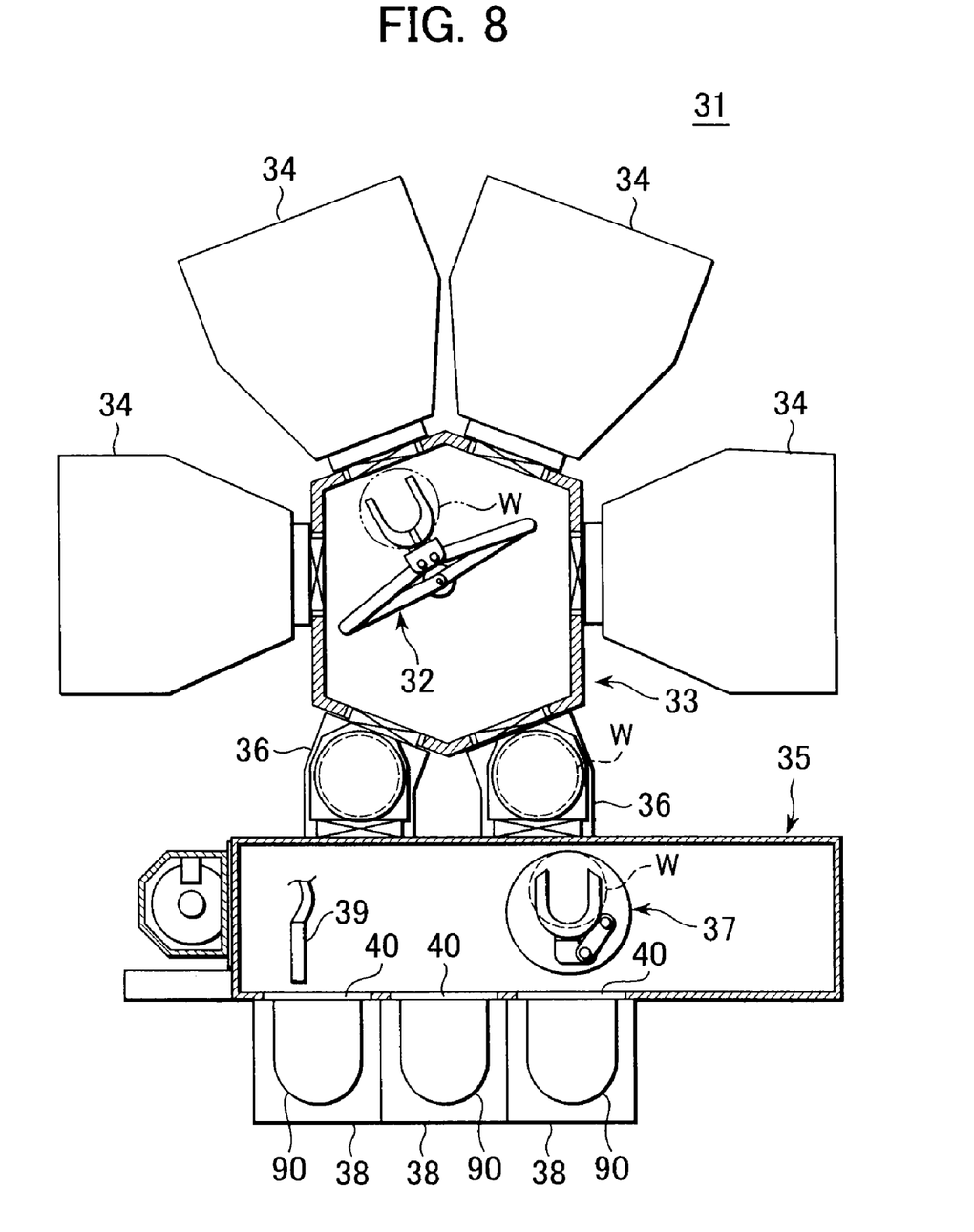
FIG. 8 is a plan view schematically showing the construction of a substrate processing system according to a second embodiment of this invention.

FIG. 8 schematically shows in plan view the construction of the substrate processing system of this embodiment.

As shown in FIG. 8, the substrate processing system 31 includes a transfer module 33 formed into a hexagonal shape in plan and having a transfer arm 32 disposed therein, four process modules 34 (substrate processing apparatuses) disposed radially around the transfer module 33, a loader module 35 (substrate receiving apparatus) formed into a rectangular shape in plan and having a transfer arm 37 disposed therein, and two load lock modules 36 interposed between the transfer module 33 and the loader module 35.

Each of the process modules 34 performs, on a wafer W, predetermined processing such as etching, CVD, thermal treatment, diffusion processing, or substrate cleaning. By using the transfer arm 32, the transfer module 33 transfers a wafer W into and out from each of the process modules 34 or the load lock modules 36.

The loader module 35 includes three FOUP mounting tables 38 disposed on a side surface thereof which is opposite from a side surface on which the load lock modules 36 are connected, and also includes three openings 40 corresponding to respective ones of the FOUP mounting tables 38. The openings 40 are each formed into the same shape as the opening 13 of the FOUP inspection apparatus 10 shown in FIG. 1. When the FOUP 90 is placed on one of the FOUP mounting tables 38 and connected to the loader module 35, the lid 92 of the FOUP 90 is able to enter inside the loader module 35. The lid 92 entering inside the loader module 35 is removed from the FOUP 90 by an FOUP opener, which is the same in construction as the FOUP opener 14 of the FOUP inspection apparatus 10. As a result, the inside of the FOUP 90 is communicated with the inside of the loader module 35. The transfer arm 37 transfers a wafer W into or out from the FOUP 90 or any one of the load lock modules 36.

The loader module 35 includes a probe nozzle 39 that includes therein a particle-separation promoting nozzle and a particle collecting nozzle. The probe nozzle 39 has the same construction as that of the probe nozzle 15 of the FOUP inspection apparatus 10, is adapted to enter inside the FOUP 90, and is disposed to face the measurement object part inside the FOUP 90.

The substrate processing system 31 includes an exhaust apparatus (corresponding to the exhaust apparatus 50 in FIG. 2). The exhaust apparatus is connected to the particle collecting nozzle of the probe nozzle 39 via a pipe in which a moisture trap, a particle counter (measurement unit), and a particle trap are disposed (none of which is shown). When gas, etc. inside the FOUP 90 are evacuated by the exhaust apparatus via the pipe and the particle collecting nozzle, the particle collecting nozzle sucks floating particles inside the FOUP 90 together with gas, and collects the particles.

In the substrate processing system 31, the inside of the FOUP 90 is communicated with the inside of the loader module 35, a wafer W housed in the FOUP 90 is transferred into one of the process modules 34 via the loader module 35, one of the load lock modules 36, and the transfer module 33. During the wafer W being subjected to predetermined processing, the probe nozzle 39 enters inside the FOUP 90 from which the wafer W has been transferred out, and the particle-separation promoting nozzle of the probe nozzle 39, which is disposed to face the measurement object part inside the FOUP 90, injects heated gas mixed with water vapor toward the measurement object part at a low speed, to thereby promote the separation of particles from the measurement object part. The particle collecting nozzle sucks and collects particles separated from the measurement object part. A particle counter, having the same construction as that of the particle counter 23 of the FOUP inspection apparatus 10, measures an amount of particles collected by the particle collecting nozzle and then flowing through the pipe.

With the substrate processing system 31 of this embodiment, the particle-separation promoting nozzle and the particle collecting nozzle of the probe nozzle 39 enter inside the FOUP 90 to promote the particle separation, the separated particles are collected, and an amount of the collected particles is measured by the particle counter, whereby an amount of particles adhered to the inner wall of the FOUP 90 and to the carriers 94 disposed therein can be measured with accuracy.

The loader module 35 includes the probe nozzle 39 having the particle-separation promoting nozzle and the particle collecting nozzle and able to enter inside the FOUP 90. Thus, the amount of particles adhered to the inner wall, etc. can be measured, with the FOUP 90 kept connected to the loader module 35. As a result, the amount of particles can be measured while the process module 34 is performing processing on a wafer W transferred out from the FOUP 90 by the loader module 35, thus making it possible to efficiently carry out the measurement.

In the above described embodiment, the FOUP P in which wafers W are housed is the object of measurement of particles P, however, the measurement object is not limited thereto and may be another type of container, stocker, or storage for housing wafers W.

What is claimed is:

1. A container cleanliness measurement apparatus comprising:
   a separation promoting unit adapted to promote separation of particles;
   a collection unit adapted to collect separated particles
   a measurement unit adapted to measure an amount of collected particles; and
   a lid holder adapted to open and close a lid of a container which is adapted to house substrates,
   wherein said lid holder opens the lid so that said separation promoting unit and said collection unit enter inside the container.

2. The container cleanliness measurement apparatus according to claim 1, wherein said separation promoting unit and said collection unit are each formed into an elongated nozzle shape having an opening formed therein.

3. The container cleanliness measurement apparatus according to claim 2, wherein the opening of said collection unit is formed to surround the opening of said separation promoting unit.

4. The container cleanliness measurement apparatus according to claim 3, wherein said collection unit has a pipe shape, and an outer diameter of said collection unit is set 1 cm to 2 cm.

5. The container cleanliness measurement apparatus according to claim 2, wherein said separation promoting unit and said collection unit have pipe shapes, and said separation promoting unit and said collection unit has nearly the same in diameter, and are disposed side-by-side.

6. The container cleanliness measurement apparatus according to claim 2, wherein said separation promoting unit and said collection unit are integrally constituted as a shower head.

7. The container cleanliness measurement apparatus according to claim 1, wherein said separation promoting unit is adapted to inject at least water vapor.

8. The container cleanliness measurement apparatus according to claim 7, wherein said collection unit is connected to an exhaust apparatus, and a moisture collection unit is disposed between said collection unit and said exhaust apparatus.

9. The container cleanliness measurement apparatus according to claim 1, wherein said separation promoting unit is adapted to inject heated gas.

10. The container cleanliness measurement apparatus according to claim 1, wherein said separation promoting unit is adapted to inject a substance with two possible phase states of gas and liquid phases or of gas and solid phases.

11. The container cleanliness measurement apparatus according to claim 1, wherein said separation promoting unit is adapted to inject gas while varying a flow speed of the gas to make the gas act as a pulsed wave.

12. The container cleanliness measurement apparatus according to claim 1, wherein said separation promoting unit and said collection unit are adapted to scan a region of a predetermined area.

13. The container cleanliness measurement apparatus according to claim 1, wherein said measurement unit is adapted to observe scattered light generated by laser light irradiation onto the collected particles.

14. The container cleanliness measurement apparatus according to claim 1, wherein said measurement unit includes a flow path adapted to permit the collected particles to flow therethrough and having a bent portion, and a pressure-sensitive device disposed in the bent portion of the flow path so as to face a flow of an exhaust including the particles.

15. The container cleanliness measurement apparatus according to claim 1, wherein said separation promoting unit promotes particle separation by injecting a cleaning substance including a gas to a surface of a measurement object part at a speed in which a boundary layer is not produced thereon.

16. A substrate processing system including a substrate receiving apparatus adapted to receive substrates by being connected with a container which is adapted to house the substrates, and a substrate processing apparatus adapted to perform processing on the received substrates, wherein:
    said substrate receiving apparatus includes a separation promoting unit adapted to promote separation of particles, a collection unit adapted to collect separated particles, and a lid holder adapted to open and close a lid of the container;
    the lid holder opens the lid so that said separation promoting unit and said collection unit enter inside the container connected to said substrate receiving apparatus; and
    the substrate processing system further includes a measurement unit adapted to measure an amount of collected particles.

17. The substrate processing system according to claim 16, wherein said substrate processing apparatus is adapted to perform any one of etching, CVD, heat treatment, diffusion processing, and substrate cleaning.

\* \* \* \* \*